United States Patent [19]
Andoh et al.

[11] 4,329,492
[45] May 11, 1982

[54] PROCESS FOR PRODUCTION OF METHACRYLIC ACID ESTERS

[76] Inventors: Naoki Andoh, 1, Morigayama-cho; Itsuo Nishiwaki, 2114, Yamanoishilei-cho; Masatoshi Arakawa, 1, Morigayama-cho, all of Yokkaichi City, Mie Prefecture, Japan

[21] Appl. No.: 209,032

[22] Filed: Nov. 21, 1980

Related U.S. Application Data

[63] Continuation of Ser. No. 49,435, Jun. 18, 1979, which is a continuation-in-part of Ser. No. 951,191, Oct. 13, 1978, abandoned, which is a continuation of Ser. No. 817,182, Jul. 20, 1977, abandoned.

[30] Foreign Application Priority Data

Jul. 27, 1977 [JP] Japan ................................ 51/94473

[51] Int. Cl.³ ............................................. C07C 67/08
[52] U.S. Cl. ................................................. 560/205
[58] Field of Search .............................. 560/205, 218

[56] References Cited

U.S. PATENT DOCUMENTS 2,406,561  8/1946  Rehberg .............................. 560/218
3,875,212  4/1975  Ohrui et al. ......................... 560/205

OTHER PUBLICATIONS

Kirk–Othmer, "Encyclopedia of Chemical Technology", Interscience Publ., 2nd Ed., (1966), vol. 8, pp. 719–721.

Primary Examiner—Natalie Trousof
Assistant Examiner—L. Hendriksen
Attorney, Agent, or Firm—Wyatt, Gerber, Shoup, Scobey & Badie

[57] ABSTRACT

A continuous process for producing methacrylic acid ester from methacrylic acid and a lower alcohol containing 1 to 3 carbon atoms utilizing sulfuric acid as a catalyst and a hydrophobic solvent to assist in the formation of a heterogeneous reaction mixture, the process being particularly characterized by the steps of reconcentrating and reusing the sulfuric acid.

11 Claims, 2 Drawing Figures 4,329,492

PROCESS FOR PRODUCTION OF METHACRYLIC ACID ESTERS

RELATED APPLICATIONS

This is a continuation, of/application Ser. No. 049,435 filed June 18, 1979 which is in turn a continuation in part of application Ser. No. 951,191 filed Oct. 13, 1978 which is, in turn, a continuation of application Ser. No. 817,182 filed July 20, 1977 the latter two of which are now abandoned.

BACKGROUND OF THE INVENTION

1. Field of the Invention

This invention relates to a process for producing methacrylic acid esters. More particularly, it is concerned with a continuous process for production of methacrylic acid esters in the presence of sulfuric acid as a catalyst in at least two reaction zones connected in series.

2. Description of the Prior Art

Various methods have been proposed to produce methacrylic acid esters from methacrylic acid and lower alcohols. These methods are described, for example, in British Pat. No. 1,017,806, U.S. Pat. Nos. 3,639,460, 3,639,461, Japanese Patent Publication Nos. 13964/1968, 1369/1973, 42857/1973, Japanese Patent Laid Open Nos. 124018/1974, 45020/1974, etc.

The methods described in British Pat. No. 1,017,806 and U.S. Pat. No. 3,639,461 are directed to vapor-phase esterification procedures. These methods, however, are not preferred from a commercial standpoint in that there is a danger of pipe blockages due to polymerization of methacrylic acid esters at the high reaction temperatures.

The method described in U.S. Pat. No. 3,639,460 is a so-called methacrylic acid excess method in which the molar ratio of lower alcohol to methacrylic acid present in a reactor is less than 1. It is theoretically excellent. However, various difficulties are encountered in carrying out this method since a large amount of methacrylic acid is present in a reactor at high temperatures and concentrations. This easily leads to the formation of undesirable quantities of polymers.

The other methods are directed to liquid-phase reactions, in which an excess of a lower alcohol is used. The procedures described in Japanese Patent Publication Nos. 13964/1968, 1369/1973, Japanese Patent Laid Open No. 124018/1974 use a cation exchange resin as a catalyst. Methods using a cation exchange resin as a catalyst have the advantage that handling of the reaction mixture after esterification is simplified compares to those procedures in which sulfuric acid is used as a catalyst. They are not completely satisfactory, however, since the reaction rate is low in comparison with the sulfuric acid method, and the cation exchange resin deteriorates, resulting in a gradual reduction in catalytic capability.

In the method described in Japanese Patent Publication No. 13964/1968, for example, the unreacted methacrylic acid cannot be completely recovered. When methyl methacrylate is intended to be produced effectively by the above method using a cation exchange resin as a catalyst, it is not possible to increase the conversion of methacrylic acid unless a large excess of methanol is used. In addition, it is necessary to employ severe reaction conditions, e.g., to increase the reaction rate or lengthen the reaction period. The more rigorous reaction conditions cause serious loss of methacrylic acid due to polymerization.

In Japanese Patent Publication No. 1369/1973, a method is disclosed in which acrylic acid is esterified, but there is no example showing esterification of methacrylic acid. When the same method is applied to methacrylic acid, the reaction rate decreases. In order to compensate the reduction in reaction rate, it is necessary, as described above, to increase the reaction temperature or lengthen the reaction period. As previously mentioned, however, this causes loss of methacrylic acid due to polymerization.

This fact is clearly shown in an example of Japanese Patent Laid Open No. 124018/1974, in which the esterification is carried out in the presence of a hydrocarbon at a temperature of 110° C. The temperature at which the reaction solution is separated is as high as 140° C. The temperature at which the reaction solution is separated can be somewhat decreased by effecting the separation under reduced pressure. However, it is not desirable to increase the rate of esterification by raising the reaction temperature because of the resulting heat polymerization of methacrylic acid and methacrylic acid esters.

Because of these difficulties, sulfuric acid is the most commonly used esterification catalyst. Sulfuric acid has the advantage of low cost coupled with the ability of absorbing water formed during the esterification reaction, thereby increasing the rate of esterification.

Recently, however, the costs of alkalis required for neutralizing the waste sulfuric acid after esterification have increased. Moreover, water criteria for industrial waste water have been made more stringent. It is now necessary in many areas that the waste liquor from esterification reaction be subjected to additional, and costly, purification procedures.

Thus, although the sulfuric acid method using a large amount of sulfuric acid has certain advantages, it is now losing its advantages compared to other procedures, since the disposal processing of the waste sulfuric acid is highly expensive.

SUMMARY OF THE INVENTION

An object of the present invention is to provide a process for continuously and effectively producing methacrylic acid esters from methacrylic acid and lower alcohols containing 1 to 3 carbon atoms in the presence of sulfuric acid as a catalyst without consuming a large amount of sulfuric acid and a sulfuric acid neutralizing agent.

Another object of the present invention is to provide a process for producing methacrylic acid esters which is not subject to the defects of conventional sulfuric acid methods and which produces no waste sulfuric acid.

Other objects will be apparent from this detailed description taken in conjunction with the accompanying drawings.

Accordingly, the present invention provides a continuous process for producing methacrylic acid ester from methacrylic acid and a lower alcohol containing 1 to 3 carbon atoms in the presence of sulfuric acid which comprises:

introducing methacrylic acid and a reaction inert hydrophobic organic solvent which does not form an azeotrope of the ester being prepared into the first reaction zone of a reaction system comprising at least two reaction zones connected in series, the amount of the hydrophobic organic solvent being from about 0.1 to about 5 parts by weight per part by weight of the methacrylic acid;

introducing sulfuric acid into the final reaction zone of the reaction system and the lower alcohol into any of the reaction zones;

reacting the methacrylic acid and the lower alcohol in the heterogeneous state in each reaction zone at a selected temperature for a selected period of time;

recovering an hydrophobic solvent phase containing methacrylic acid ester and a sulfuric acid phase composed mainly of sulfuric acid from each reaction zone; introducing the hydrophobic organic solvent phase into the subsequent reaction zone and the sulfuric acid phase into the preceding reaction zone;

concentrating the sulfuric acid phase withdrawn from the first reaction zone and returning it to the final reaction zone; and distilling the hydrophobic organic solvent phase withdrawn from the final reaction zone to separate methacrylic acid ester therefrom.

DETAILED DESCRIPTION OF THE INVENTION

Figure 1:
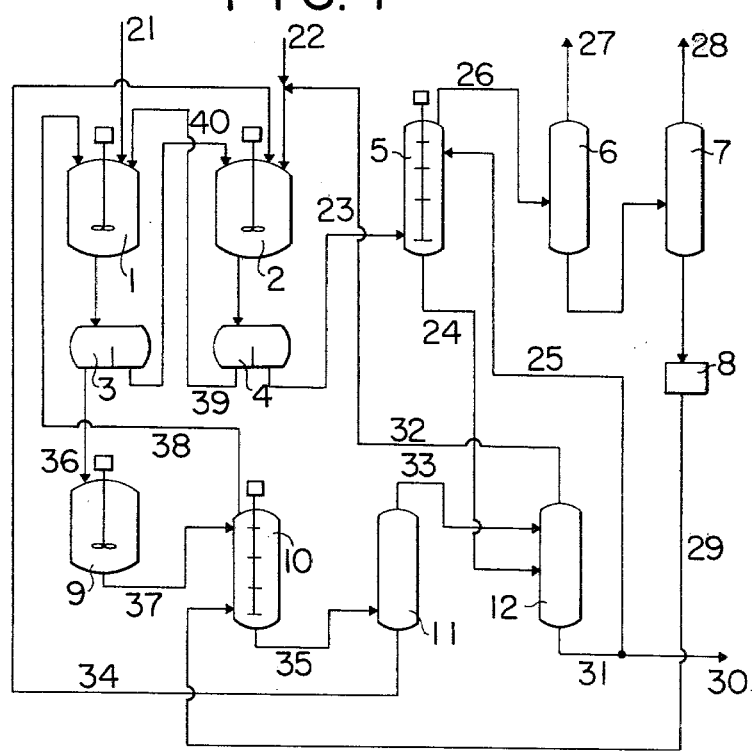
FIG. 1 is a schematic flow diagram of a preferred embodiment of the present invention.

One of the features of the present invention resides in that sulfuric acid used as an esterification catalyst is concentrated after use and reused. Thus, there is no need for processing waste sulfuric acid. In addition, no relatively expensive alkalis for neutralizing waste sulfuric acid are needed. Furthermore, since only small amounts of waste water containing organic compounds are produced, no special and costly techniques and apparatus for processing the waste water are needed.

In general, when sulfuric acid is used in an esterification reaction, it absorbs and is diluted by the water which forms as a by-product. It is necessary, therefore, to concentrate the sulfuric acid for reuse. Although the concentration of the sulfuric acid can be increased to a very high level, the limit to which the concentration can be increased economically is about 80% by weight.

In a preferred embodiment of the present invention, the sulfuric acid phase withdrawn from the first reaction zone is concentrated to a level of from about 50 to about 80% by weight and returned to the final reaction zone. This, in itself, is a marked advantage over conventional procedures which customarily employ sulfuric acid concentrations of more than 90% by weight. This particular advantage of the process may be attributed to the fact that the starting materials are contacted countercurrently.

For effecting the countercurrent reaction of the starting materials, it is necessary that the reaction mixture be in the heterogeneous state; that is to say, the reaction mixture separates into a sulfuric acid phase comprising principally sulfuric acid and a solvent phase containing the major proportion of methacrylic acid esters. It is desired that methacrylic acid dissolves as little as possible in the solvent phase, since it is difficult to separate the acid from the esters.

Another feature of the present invention is the use of a selected amount of a reaction inert, hydrophobic, organic solvent which is substantially insoluble in water and does not form an azeotropic mixture with methacrylic acid esters. It is preferred that the solvent be one which is stable to heat and oxygen. This aids in the formation of heterogeneous mixtures, and at the same time, facilitates the separation of methacrylic acid esters.

Hydrophobic organic solvents useful in this invention include; for example, saturated aliphatic hydrocarbons, saturated cyclic hydrocarbons and aromatic hydrocarbons, having a boiling point of about 0° to 250° C. Since these hydrophobic organic solvents are required not to form an azeotropic mixture with methacrylic acid esters under the conditions of the process, it is preferred that the difference between the boiling points of the hydrophobic organic solvent and methacrylic acid ester to be produced is at least about 30° C. so as to facilitate separation of a pure product by distillation.

Suitable examples of hydrophobic organic solvents which can be used in the present invention are pentane, hexane, heptane, nonane, decane, cyclopentane, cyclohexane, propylcyclohexane, ethylbenzene, xylene, cumene and the like.

In the production of methyl methacrylate, pentane, hexane, nonane, cyclopentane, propylcyclohexane, ethylbenzene, xylene, cumene and the like are preferably used.

Non-hydrophobic organic solvents containing oxygen, nitrogen, etc., in the molecule, such as ethers, ketones, esters, amines and the like are not useful in the practice of the invention because they have a high compatibility with methacrylic acid and tend to slow down the rate of esterification.

In accordance with the method of the present invention, methacrylic acid is introduced in admixture with the selected hydrophobic organic solvent or mixture of such solvents into the first reaction zone of the reaction system comprising at least two reaction zones connected in series. A lower alcohol containing 1 to 3 carbon atoms may be introduced into any of the reaction zones, e.g., into the first reaction zone in combination with methacrylic acid. It is preferred, however, that the lower alcohol is introduced into the final reaction zone in combination with sulfuric acid as a catalyst. By this procedure, the concentration of alcohol is highest in that particular reaction zone where the concentration of acid is lowest. This arrangement assists in assuring as complete a reaction of the methacrylic acid as possible and, concomitantly increases the rate of reaction.

While the use of high purity methacrylic acid is preferred, it is a particular advantage that relatively crude methacrylic acid can be employed in the process of the invention.

The lower alcohols utilized in the practice of this invention are alkanols and alkenols such as methanol, ethanol, iso-propanol, propanol, and allyl alcohol. Those alcohols containing 4 or more carbon atoms tend to resist the formation of a heterogeneous state, and thus they are not suitable for use in the present invention.

The amount of the lower alcohol employed is generally at least equimolar, based on the moles of methacrylic acid. Preferably at least 1.5 mole per mole of methacrylic acid is utilized. The use of a large excess of the lower alcohol impedes the formation of the heterogeneous reaction state. Therefore, it is customary to employ not more than 10 moles per mole of methacrylic acid, preferably not more than 5 moles.

The amount of the hydrophobic organic solvent used is from about 0.1 to 5 parts by weight per part by weight of methacrylic acid, preferably about 0.2 to 3 parts by weight. When the amount of the hydrophobic organic solvent is less than about 0.1 part by weight, it is difficult to cause the reaction mixture to become heterogeneous, and even if the heterogeneous state is achieved, the compatibility of the various components is undesirably high so that the system tends to be unstable and to return to a homogeneous state. On the other hand, the use of the hydrophobic organic solvent in an amount of more than about 5 parts by weight is undesirable because it is uneconomical. Additionally, the partition of methacrylic acid in the reaction mixture into the organic solvent phase is increased. As a result, the concentration of methacrylic acid entrained in the phase containing the methacrylic acid esters is increased and purification difficulties arise.

The concentration of sulfuric acid used in the present invention is preferably in a range of about 50 to 80% by weight. The sulfuric acid diluted with water or alcohols after esterification is concentrated in a sulfuric acid concentration column to a level of about 50 to 80% by weight for reuse. Sulfuric acid can be, if desired, purified by a means such as filtration or absorption filtration before or after the concentration.

Sulfuric acid is normally employed in an amount of about 0.1 to 10 parts by weight per part by weight of methacrylic acid, preferably about 0.15 to 5 parts by weight.

The reaction of methacrylic acid and a lower alcohol is generally carried out at a temperature of from about 0° C. to 100° C., preferably from 20° C. to 80°°C. and a pressure of from about ordinary pressure to several atmospheric pressure. At temperatures higher than about 100° C., methacrylic acid and methacrylic acid esters undergo heat polymerization, resulting in the undesired loss of product.

The time required for the esterification is generally for about 1 to about 100 hours, preferably from about 2 to about 30 hours.

In order to prevent polymerization, a suitable amount of a polymerization inhibitor may be added. Any of a large number of conventionally employed inhibitors such as hydroquinone, butylated hydroxy anisole, naphthaquinone or anthranil are suitable.

Figure 2:
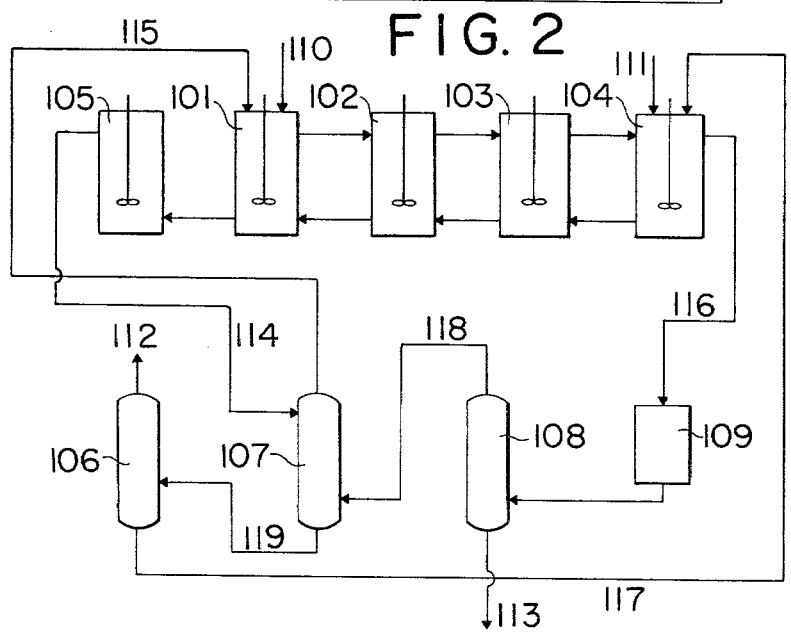
FIG. 2 is a schematic flow diagram of another preferred embodiment of the present invention.

The continuous operation of the process of this invention including recovery of a hydrophobic organic solvent phase containing methacrylic acid ester and a sulfuric acid phase composed mainly of sulfuric acid from each reaction zone can be carried out, for example, by the methods shown in FIGS. 1 and 2. That is to say, in one embodiment of the present invention, a reaction mixture is withdrawn from each reaction zone and introduced into a separator where the reaction mixture is separated into the hydrophobic organic solvent phase and the sulfuric acid phase. In another embodiment, stirring of the reaction mixture is carried out at a rate so as to maintain the reaction mixture substantially separated into the hydrophobic organic solvent phase and the sulfuric acid phase in each reaction zone. The hydrophobic organic solvent phase is withdrawn from the upper portion of each reaction zone whereas the sulfuric acid phase is withdrawn from the lower portion.

These embodiments will hereinafter be explained in more detail by reference to the accompanying drawings.

In regeneration of the sulfuric acid phase after esterification withdrawn form the first reaction zone, the sulfuric acid phase is first treated with an organic solvent as an extractant. The same hydrophobic organic solvent utilized in the principal reaction, usually after being recovered from the final reaction zone and purified, is preferably employed. In this way, a small amount of methacrylic acid and methacrylic acid esters dissolved in the sulfuric acid phase are extracted and separated.

The extraction temperature is generally from about 0° C. to 100° C., preferably from 10° C. to 50° C.

The sulfuric acid phase washed with the organic solvent is then stripped in a sulfuric acid concentration apparatus to separate a part of alcohol and water dissolved therein. The stripping is generally carried out under the conditions of ordinary pressure to reduced pressure and ambient temperature to 200° C., preferably 50° C. to 120° C.

The crude ester solution may then be passed through a water washing step, although this may be omitted. The next steps are solvent recovery and an ester purification. The preferred purification is distillation to separate the purified ester from the solvent and a small amount of impurities.

The distillation is carried out under conventional conditions selected on the basis of the boiling points of the ester and the hydrophobic organic solvent from which it is to be separated. Care should be taken not to expose methacrylic acid esters to high temperatures because they are unstable to heat.

The principal advantages of the present invention are as follows:

(1) Since sulfuric acid used as an esterification catalyst can be used repeatedly by circulating, there is no need for processing a large amount of sulfuric acid, as in the conventional methods.

(2) The amount of sulfuric acid consumed is small, so the process is economical.

(3) Since the reaction temperature is relatively low, the loss of methacrylic acid or methacrylic acid esters due to heat polymerization is limited.

(4) Since the starting materials and catalyst are contacted with each other countercurrently, the conversion is high and continuous production is possible.

(5) Since the product is extracted with an organic solvent, the yield is high.

Preferred embodiments of the present invention will now be explained by reference to the accompanying drawings.

FIG. 1 is a schematic flow diagram of an embodiment of the present invention which is particularly useful when the organic solvent has a higher boiling point than the methacrylic acid ester being produced.

Methacrylic acid, a circulating organic solvent and a reaction solution (mixed solution of sulfuric acid and alcohol) are introduced into the first reaction zone, i.e., first esterification reactor 1 through lines 21, 38 and 39, respectively.

An alcohol, circulating sulfuric acid and a reaction solution (mixed solution of methacrylic acid, methacrylic acid ester, organic solvent and the like) are introduced into the final reaction zone, i.e., second esterification reactor 2 through lines 22, 34 and 40, respectively.

A heterogeneous reaction solution withdrawn from first esterification reactor 1 is introduced into first separator 3 to effect phase-separation. An organic solvent phase of the reaction solution is fed to a second esterification reactor 2 through line 40. The sulfuric acid phase is fed to auxiliary esterification reactor 9 through line 36 where it is used to further increase the conversion.

A heterogeneous reaction solution withdrawn from second esterification reactor 2 is introduced into second separator 4 to permit phase-separation. An organic solvent phase is fed to water-washing column 5 through line 23 and a sulfuric acid phase is returned to first esterification reactor 1 through line 39.

Water is introduced into water-washing column 5 through line 25 provided at the upper portion thereof and is countercurrently contacted with a crude ester solution introduced through line 23 provided at the lower portion thereof to extract the alcohol and methacrylic acid in the reaction solution. The ester solution after water washing is introduced into first distillation column 6 through line 26 from which a small amount of low boiling impurities (e.g., methyl acetate, methyl acrylate, methanol, etc.) are withdrawn through line 27. The ester solution is fed to second distillation column 7 where a high boiling component containing the high boiling organic solvent is separated, and purified methacrylic acid ester is recovered through line 28.

The organic solvent recovered is purified by passing through filter or polymer removing equipment 8 and fed through line 29 to sulfuric acid solution washing column 10 where it is used as an extractant.

The reaction solution withdrawn from auxiliary esterification reactor 9 is fed to sulfuric acid solution washing column 10 through line 37 where an organic solvent-soluble component is extracted with the organic solvent acting as an extractant and recovered. The remaining solution composed mainly of sulfuric acid is introduced into sulfuric acid concentration column 11 and heated under reduced pressure to distill away those compounds dissolved therein such as methanol and a part of water. The concentrated sulfuric acid is returned through line 34 to second esterification reactor 2.

Waste water withdrawn from water washing column 5 is fed to alcohol recovering column 12 where it is heated in combination with the distillate fed from sulfuric acid concentration column 11 through line 33 to separate a component composed mainly of alcohol. This component is then returned to second esterification reactor 2. The remaining water is withdrawn through line 31. A part of the remaining water withdrawn is fed to water-washing column 5 through line 25, and the remainder is taken out as waste water through line 30.

FIG. 2 is a schematic flow diagram of another preferred embodiment of the present invention. The principal difference between the embodiment shown in FIG. 1 and this embodiment shown is that the separators 3 and 4 used in the first system are omitted. In other respects, they are materially the same, although several modifications are made.

In the system of FIG. 2, methacrylic acid and a solvent are introduced into first esterification reactor 101 through lines 110 and 115, respectively. Alcohol and sulfuric acid are introduced into the fourth esterification reactor 104 through lines 111 and 117, respectively.

In each esterification reactor, stirring of the reaction solution is carried out under conditions such that the reaction mixture is separated substantially into two layers, an upper layer and a lower layer. The upper layer, i.e., organic solvent layer, is circulated from first esterification reactor 101 through second esterification reactor 102 and third esterification reactor 103 to fourth esterification reactor 104. The lower layer, i.e., sulfuric acid layer, is circulated from fourth esterification reactor 104 through third esterification reactor 103, second esterification reactor 102 and first esterification reactor 101 to auxiliary esterification reactor 105.

A crude ester solution is withdrawn through line 116 and introduced into filter or polymer removing apparatus 109 where the crude ester solution is purified. This ester solution is then introduced into solvent recovery and ester purification apparatus 108 in which the solvent is separated and recovered, and from which an ester is recovered through line 113.

The sulfuric acid solution withdrawn from auxiliary esterification reactor 105 is introduced through line 114 into sulfuric acid solution washing column 107 where the sulfuric acid solution is washed by countercurrently contacting with the solvent introduced thereinto through line 118 and then it is introduced into sulfuric acid concentration column 106 through line 119.

The sulfuric acid solution is stripped in sulfuric acid concentration column 106 by heating. The unreacted alcohol, water and other volatile compounds are recovered through line 112 and the bottoms are returned through line 117 to fourth esterification reactor 104.

The recovered solvent separated from the ester is introduced into sulfuric acid solution washing column 107 through line 118 and used to extract a part of organic materials contained in the sulfuric acid solution. The recovered solvent is then introduced into first esterification reactor 101 through line 115. It will be apparent that, while at least two reactors must be employed in the practice of this invention, the actual number employed may be very high. For some large scale industrial operations 10 or more reactors may be utilized. For most practical purposes, however, 3 to 6 reactors will be preferred.

The following non-limiting examples are given by way of illustration only. In the examples, all percents are by weight unless otherwise indicated.

EXAMPLE 1

Except that the sulfuric acid stripping and concentrating units were closed off, this example was carried out utilizing the system illustrated in the flow diagram shown in FIG. 2; that is, five acid resistant reactors (capacity: 2 liters) provided with a temperature controller and a stirrer were used as esterification reactors. Four of them were provided with nozzles, one at the bottom and a second at a position of $\frac{2}{3}$ of their height and were connected as shown in FIG. 2 by means of polyethylene pipes having a diameter of 10 mm.

Sulfuric acid solution washing column 107 was a SUS-314 stainless steel pipe of an inner diameter of 21 mm and a length of 3 m which was filled with $\frac{1}{4}$ inch Raching rings. The lowest portion of sulfuric acid solution washing column 107 was so designed that it was possible to view the interface, and thus the sulfuric acid solution could be withdrawn while observing the interface.

The proportion of an upper solution to a lower solution in each esterification reactor can be controlled by controlling the height of a nozzle for withdrawing the lower solution which is provided to auxiliary esterification reactor 105, and in this example, the proportion was 1:1.

Into first esterification reactor 101 were introduced 300 g/hr of methacrylic acid and 150 g/hr of n-hexane as a hydrophobic organic solvent. A total of 220 g/hr of methanol and 110 g/hr of fresh 70% sulfuric acid as sulfuric acid were introduced into the fourth esterification reactor 104. The reaction was carried out during a stay time in the reaction system of about 6 hours, and at a temperature of 50° C.

The calculations are shown in Table 1.

The volume of each reactor is 2 liters. However, the lateral pipe is at a position two thirds of the distance from the base to the top. Accordingly, the effective inner volume will be $\frac{2}{3} \times 2$. or 1.33 liters.

TABLE 1

| Feed | Density | g/hr | ml/hr |
|---|---|---|---|
| MMA | 1.01 | 300 | 297 |
| HEXANE | 0.66 | 150 | 227 |
| METHANOL | 0.79 | 220 | 278 |
| 70% H$_2$SO$_4$ | 1.61 | 110 | 68 |
| TOTAL | | 780 | 870 |

Stay Time Based on 4 Reactors $$\frac{1.33 \times 4l}{0.87 \, l/hr} = 6.11 \, hr$$

After a lapse of 200 hours, a crude ester solution in line 116 and a sulfuric acid solution in line 114 were analyzed.

The flow rate of the crude ester solution was about 520 g/hr, and it contained 65.0% methyl methacrylate, 1.62% methacrylic acid and 28.5% n-hexane. The flow rate of the sulfuric acid solution was about 260 g/hr, and it contained 0.35% methyl methacrylate and 0.23% methacrylic acid.

For these results, it can be seen that the yield of methyl methacrylate was 97.3 mole % based on methacrylic acid and 99.7% of the methyl methacrylate obtained was contained in the crude ester solution. Methyl methacrylate recovered from the crude ester solution was 97.0 mole % based on methacrylic acid.

EXAMPLE 2

The procedure of Example 1 was repeated with the exception that n-nonane was used as a solvent and the reaction temperature was 60° C. Additionally, the sulfuric acid concentrating and stripping systems of FIG. 2 were utilized. After a lapse of 150 hours, a crude ester solution in line 116 and a sulfuric acid solution in line 114 were analyzed.

The flow rate of the crude ester solution was about 520 g/hr, and it contained 65.2% methyl methacrylate, 1.48% methacrylic acid and 28.1% n-nonane. The flow rate of the sulfuric acid solution was about 260 g/hr, and it contained 0.38% methyl methacrylate and 0.27% methacrylic acid.

For these results, it can be seen that the yield of methyl methacrylate was 97.2 mole % and 99.7% of the methyl methacrylate obtained was contained in the crude ester solution.

EXAMPLE 3

The procedure of Example 2 was repeated with the exception that ethylbenzene was used as a solvent and the reaction temperature was 60° C. After a lapse of 100 hours, the same analysis as in Example 1 was conducted.

The flow rate of the crude ester solution was about 515 g/hr, and it contained 65.3% methyl methacrylate, 1.76% methacrylic acid and 28.1% ethyl benzene. The flow rate of the sulfuric acid solution was about 265 g/hr, and it contained 0.25% methyl methacrylate and 0.19% methacrylic acid.

From these results, it can be seen that the yield of methyl methacrylate was 96.7%, and 99.8% of the methyl methacrylate obtained was contained in the crude ester solution.

The following experiments were conducted to assist in explaining and understanding the invention, and to illustrate the significance of certain of the process parameters.

EXPERIMENT 1

This experiment establishes that the sulfuric acid can be stripped, concentrated and used repeatedly in a continuous manner.

The sulfuric acid solution obtained in Example 1 was subjected to stripping at a reduced pressure of 20 mm Hg at a bottom temperature of 70° C. The amount of the sulfuric acid solution was reduced from 2.0 Kg to 0.76 Kg. The solution from the bottom of the column was colorless and transparent, and sulfuric acid having a specific density of 1.59 (at room temperature) and a concentration of 70% was obtained.

The procedure of Example 1 was repeated with the exception that the sulfuric acid obtained by repeating the above processing was used in place of fresh 70% sulfuric acid. After a lapse of 150 hours, a crude ester solution in line 116 and a sulfuric acid solution in line 114 were analyzed.

The flow rate of the crude ester solution was about 520 g/hr, and it contained 64.5% methyl methacrylate, 1.70% methacrylic acid and 28.5% n-hexane.

The flow rate of the sulfuric acid solution was about 260 g/hr, and it contained 0.35% methyl methacrylate and 0.25% methacrylic acid.

From these results, it can be seen that the yield of methacrylic acid ester was 96.5 mole % based upon methacrylic acid, and 99.7% of the methacrylic acid ester obtained was contained in the crude ester solution.

EXPERIMENT 2

A 300 ml flask was charged with 43.0 g of methacrylic acid, 31.5 g of methanol, 21.5 g of n-hexane and 15.8 g of 70% sulfuric acid, which were fully stirred and reacted at 50° C. for 10 hours. The ratio of the starting materials used was the same as in Example 1. After the reaction was completed, the amounts of upper and lower layers and the methyl methacrylate concentration in each layer were measured. The yield of methyl methacrylate was 91.6 mole %.

Subsequently, a 300 ml flask was charged with 43 g of methacrylic acid, 31.5 g of methanol and 15.8 g of 70% sulfuric acid, which were reacted at 50° C. for 10 hours. In this case, although the reaction system was homogenous at the beginning, when the esterification proceeded well enough, it became heterogeneous. After the reaction was completed, the yield of methyl methacrylate was measured. The yield was 91.3 mole %.

From these experiments carried out in a flask, it can be seen that esterification is not materially hindered by the presence of n-hexane. At the same time, the comparison of Experiment 2 with Example 1 indicates that where the same materials are used, if esterification is carried out countercurrently, the yield will markedly increase.

EXPERIMENT 3

Although the procedure of Example 1 was attempted without using n-hexane, immediately after the feed is introduced and heated, the reaction system became homogeneous and the countercurrent reaction became impossible.

Therefore, the line from first esterification reactor 101 to auxiliary esterification reactor 105 was closed, and methacrylic acid, methanol and 70% sulfuric acid were introduced into first esterification reactor 101 in the same amounts as in Example 1. After the reaction was continued for 100 hours, an effluent from the fourth esterification reactor was analyzed. The yield of methyl methacrylate was found to be 90.3 mole %.

From the comparison of this Experiment 3 with Example 1, it can be seen that the countercurrent reaction using the heterogeneous phase as used in Example 1 is quite useful.

EXPERIMENT 4

The procedure of Example 3 was repeated with the exception that n-butyl ether which is not a hydrophobic solvent was used in place of ethyl benzene. After a lapse of 100 hours, the same analysis as in Example 3 was conducted.

The flow rate of the crude ester solution was about 500 g/hr, and it contained 59.8% methyl methacrylate and 5.14% methacrylic acid. The flow rate of the sulfuric acid solution was about 280 g/hr in flow rate, and it contained 6.5% methyl methacrylate and 0.40% methacrylic acid.

The yield of methyl methacrylate was only 91.0 mole %, and 94.2% of the methyl methacrylate was contained in the crude ester solution. The methyl methacrylate recovered from the crude ester solution was only 85.7 mole % based upon methacrylic acid.

EXPERIMENT 5

It is considered that of the reactors used in Example 1, i.e., shown in FIG. 2, the reaction mixture most liable to become homogeneous would be in the final reactor, i.e., the fourth esterification reactor, where the concentrations of alcohol and ester are high and the concentration of water is low.

Thus, assuming that esterificaton proceeds in a high yield of substantially 100%, the following experiment was conducted to discover good hydrophobic organic solvents for use in the invention.

Assuming that 43 g (0.5 mole) of methacrylic acid was completely (100%) esterified, each solvent was added to 50 g (0.5 mole) of methyl methacrylate, 32 g (1 mole) of methanol and 16.1 g of 70% sulfuric acid, in an amount of 0, 1, 2, 5 or 100 g. The resulting mixture was agitated at room temperature, and then the state of the mixture was examined. In the absence of a solvent, the mixture was homogeneous. The results are shown in Table 2.

These results indicate that hydrophilic solvents such as esters, ketones, halides, and the like, inhibit the formation of a heterogeneous state, and even when the heterogeneous state is formed, it is expected that the compatibility is great. Thus, it has been found that hydrophilic solvents are not suitable for us in effecting countercurrent contacting.

TABLE 2

| Solvent | Amount | | | |
|---|---|---|---|---|
| | 1 g | 2 g | 5 g | 100 g |
| n-Hexane | − | + | + | + |
| n-Nonane | + | + | + | + |
| Ethylcylohexane | + | + | + | + |
| Ethylbenzene | − | + | + | + |

TABLE 2-continued

| Solvent | Amount | | | |
|---|---|---|---|---|
| | 1 g | 2 g | 5 g | 100 g |
| Chlorobenzene | − | − | + | + |
| Isopropyl Bromide | − | − | − | + |
| Ethyl Ether | − | − | − | + |
| n-Butyl Ether | − | − | + | + |
| Methyl Ethyl Ketone | − | − | − | − |
| Methyl Isobutyl Ketone | − | − | − | − |

What is claimed is:

1. A continuous process for producing methacrylic acid esters from a hetergeneous reaction mixture containing methacrylic acid, a lower alcohol containing 1 to 3 carbon atoms, and sulfuric acid as a catalyst in a plurality of reaction zones in which the reaction product water is removed from the reaction mixture to improve the production of methacrylic acid ester, said process comprising:
   a. introducing methacrylic acid and a reaction inert, hydrophobic organic solvent in which the ester being produced is soluble, the solvent being further characterized by inability to form an azeotrope with the said ester, into the first reaction zone of a reaction system comprising at least three reaction zones connected in series, the amount of the hydrophobic organic solvent being from about 0.1 to about 5 parts by weight per part by weight of the methacrylic acid;
   b. introducing sulfuric acid at a concentration of from 50% to 80% by weight into the final reaction zone of the reaction system and the lower alcohol into any of the reaction zones;
   c. reacting the methacrylic acid and the lower alcohol in a reaction mixture which is in the heterogeneous state in each reaction zone by maintaining the reaction mixture at a temperature of from about 0° C. to 100° C. for about 1 to 100 hours;
   d. recovering and separating a hydrophobic organic solvent phase containing methacrylic acid ester and a sulfuric acid phase composed mainly of sulfuric acid and water from each reaction zone;
   e. introducing each hydrophobic organic solvent phase except that recovered from the last reaction zone into the subsequent reaction zone and each sulfuric acid phase, except that recovered from the first reaction zone into the preceding reaction zone;
   f. removing water from the sulfuric acid phase withdrawn from the first reaction zone to produce sulfuric acid at a concentration of from 50% to 80% by weight and returning it to the
   final reaction zone as aforesaid in Step b.; and distilling the hydrophobic organic solvent phase withdrawn from the final reaction zone to separate methacrylate acid ester therefrom.

2. A process as in claim 1, wherein the lower alcohol is methanol.

3. A process as in claim 1, wherein the hydrophobic organic solvent is selected from the group consisting of aliphatic hydrocarbons, saturated cyclic hydrocarbons and aromatic hydrocarbons, having a boiling point of about 0° to 250° C.

4. A process as in claim 3, wherein the solvent is selected from the group consisting of pentane, hexane, heptane, nonane, decane, cyclopentane, cyclohexane, propylcyclohexane, ethylbenzene and cumene.

5. A process as in claim 3, wherein the ester is methyl methacrylate and the solvent is selected from the group consisting of pentane, hexane, nonane, cyclopentane, propylcyclohexane, ethylbenzene, xylene and cumene.

6. A process as in claim 1, wherein the lower alcohol is introduced into the final reaction zone in admixture with sulfuric acid.

7. A process as in claim 1, wherein the reaction solution withdrawn from each reaction zone is introduced into a separator, separated into and recovered as a hydrophobic organic solvent phase containing methacrylic acid ester and a sulfuric acid phase containing principally sulfuric acid, and the separate phases recovered.

8. A process as in claim 1, wherein the reaction mixture is stirred at such a rate that it is separated into an upper layer and a lower layer, which are, respectively, a hydrophobic organic solvent phase and a sulfuric acid phase.

9. A process as in claim 1, wherein the sulfuric acid phase recovered from the first reaction zone is concentrated to a sulfuric acid concentration of from 50 to 80% by weight.

10. A process as in claim 1 wherein the reaction between the methacrylic acid and the lower alcohol takes place in the presence of a polymerization inhibitor.

11. A process as in claim 10, wherein the polymerization inhibitor is hydroquinone.

* * * * *

UNITED STATES PATENT AND TRADEMARK OFFICE
CERTIFICATE OF CORRECTION

PATENT NO. : 4,329,492
DATED : May 11, 1982
INVENTOR(S) : NAOKI ANDOH ET AL

It is certified that error appears in the above—identified patent and that said Letters Patent is hereby corrected as shown below:

On the title page,

Change "[30] Foreign Application Priority Data July 27, 1977 JP Japan 51/94473" to read ---[30] Foreign Application Priority Data August 10, 1976 JP Japan 51/94473---

On the title page, Insert ---[73] JAPAN SYNTHETIC RUBBER CO., LTD. TOKYO, JAPAN

Signed and Sealed this

Thirtieth Day of November 1982

[SEAL]

Attest:

GERALD J. MOSSINGHOFF

*Attesting Officer*     *Commissioner of Patents and Trademarks*